US006485464B1

United States Patent
Christenson et al.

(10) Patent No.: US 6,485,464 B1
(45) Date of Patent: Nov. 26, 2002

(54) REDUCED HEIGHT IMPLANTABLE DRUG INFUSION DEVICE

(75) Inventors: Steven R. Christenson, Coon Rapids, MN (US); Reginald D. Robinson, Plymouth, MN (US); Kenneth T. Heruth, Edina, MN (US); James Randall, Coon Rapids, MN (US); Manfred K. Lüedi, Köniz (CH); Christian Pèclat, Neuchatel (CH)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/560,173

(22) Filed: Apr. 28, 2000

(51) Int. Cl.7 .............................................. F04B 43/12
(52) U.S. Cl. .................................... 604/153; 417/477.1
(58) Field of Search ........................ 417/477.1; 604/153

(56) References Cited

U.S. PATENT DOCUMENTS

| 2,920,578 A | 1/1960 | Schaurte | |
|---|---|---|---|
| 3,918,453 A | 11/1975 | Leonard | |
| 3,990,444 A | 11/1976 | Vial | |
| 4,012,177 A | 3/1977 | Yakich | 417/477 |
| 4,256,437 A | 3/1981 | Brown | 417/45 |
| 4,479,797 A | * 10/1984 | Kobayashi et al. | 604/153 |
| 4,525,164 A | 6/1985 | Loeb et al. | 604/131 |
| 4,545,774 A | 10/1985 | Weber et al. | 417/475 |
| 4,576,556 A | 3/1986 | Thompson | 417/477 |
| 4,650,471 A | 3/1987 | Tamari | 604/153 |
| 4,685,902 A | 8/1987 | Edwards et al. | 604/153 |
| 4,692,147 A | 9/1987 | Duggan | 604/93 |
| 4,950,136 A | 8/1990 | Haas et al. | 417/477 |
| 5,064,358 A | 11/1991 | Calarai | 417/475 |
| 5,082,429 A | 1/1992 | Soderquist et al. | 417/477 |
| 5,083,908 A | 1/1992 | Gagnebin et al. | 417/477 |
| 5,096,393 A | 3/1992 | Van Steenderen et al. | 417/477 |
| 5,213,483 A | 5/1993 | Flaherty et al. | 417/477 |
| 5,266,013 A | 11/1993 | Aubert et al. | 417/474 |
| 5,578,001 A | 11/1996 | Shah | 604/31 |
| 5,840,069 A | 11/1998 | Robinson | 604/131 |
| 6,036,459 A | 3/2000 | Robinson | 417/477 |
| 6,264,634 B1 | * 7/2001 | Yamazaki | 604/153 |

FOREIGN PATENT DOCUMENTS

| GB | 681 | 5/1902 |
|---|---|---|
| DE | 3737023 | 7/1988 |
| SU | 547550 | 2/1977 |

\* cited by examiner

*Primary Examiner*—Gerald A. Michalsky
(74) *Attorney, Agent, or Firm*—Gregory J. Cohan; Banner & Witcoff, Ltd.

(57) ABSTRACT

An implantable drug infusion device includes a pumphead assembly and a motor assembly operably connected to the pumphead assembly. The motor assembly is adjacent to and laterally offset from the pumphead assembly, advantageously reducing the overall height of the implantable drug infusion device.

26 Claims, 5 Drawing Sheets

REDUCED HEIGHT IMPLANTABLE DRUG INFUSION DEVICE

RELATED APPLICATIONS

The following applications are related to the present application: "Implantable Drug Delivery Device with Peristaltic Pump Having a Bobbin Roller Assembly", assigned Ser. No. 09/835,208, and "Implantable Drug Delivery Device with Peristaltic Pump Having a Retracting Roller", assigned Ser. No. 09/834,874, both of which were filed on Apr. 13, 2001.

BACKGROUND OF THE INVENTION

1. Field of the Invention

The present invention relates to an implantable drug delivery device for infusing a therapeutic agent into an organism, and more particularly, relates to an improved orientation of the motor assembly and pumphead assembly of an implantable drug delivery device, providing a low profile.

2. Description of the Related Art

Implantable drug infusion devices are well known in the art. These devices typically include a medication reservoir within a generally cylindrical housing. Some form of fluid flow control is also provided to control or regulate the flow of fluid medication from the reservoir to the outlet of the device for delivery of the medication to the desired location in a body, usually through a catheter. These devices are used to provide patients with a variable and prolonged dosage or infusion of a drug or other therapeutic agent.

Active drug infusion devices feature a pump or a metering system to deliver the drug into the patient's system. An example of such a drug infusion pump currently available is the Medtronic SynchroMed programmable pump. Additionally, U.S. Pat. Nos. 4,692,147 (Duggan), 5,840,069 (Robinson), and 6,036,459 (Robinson), each assigned to Medtronic, Inc., Minneapolis, Minn., and each of which disclose a body-implantable electronic drug administration device comprising a peristaltic (roller) pump for metering a measured amount of drug in response to an electronic pulse generated by control circuitry associated within the device. These patents are incorporated herein by reference in their entirety. Such pumps typically include a drug reservoir, a fill port, a peristaltic pump having a motor and a pumphead to pump out the drug from the reservoir, and a catheter port to transport the drug from the reservoir via the pump to a patient's anatomy. The drug reservoir, fill port, peristaltic pump, and catheter port are generally held in a housing, or bulkhead. The bulkhead typically has a series of passages extending from the drug reservoir and through the peristaltic pump that lead to the catheter port, which is typically located on the side of the housing.

The prior art delivery devices, however, are limiting in that they are relatively large. When a relatively large drug delivery device is implanted in a patient's body, the patient is obviously well aware of its presence and may, as a result, suffer considerable discomfort and anxiety. Additionally, large implantable devices are difficult to implant in children and small adults and require larger surgical incisions. Other problems can arise from the use of large implantable devices, including skin erosion.

In prior art implantable drug infusion devices, the bulkhead includes a pump chamber. A motor and corresponding drive assembly for operating the pump are positioned directly above the pump. One serious disadvantage of this configuration is the height of these devices. For example, the motor/pumphead in the SynchroMed device has an overall height of approximately 10.7 mm. Because implantable devices are typically implanted subcutaneously and may be implanted in a patient for many years, it has always been an objective in the design of such devices that they be as small and lightweight as possible. Size and weight are critical factors with respect to the physical and psychological comfort of the patient. Thus, it is desirable to provide an implantable drug infusion device having a smaller size, and, particularly, a reduced height and reduced total device volume.

It is an object of the present invention to provide an implantable drug infusion device which reduces or wholly overcomes some or all of the difficulties inherent in prior known devices. Particular objects and advantages of the invention will be apparent to those skilled in the art, that is, those who are knowledgeable or experienced in this field of technology, in view of the following disclosure of the invention and detailed description of preferred embodiments.

SUMMARY OF THE INVENTION

The present invention provides an implantable drug infusion device which features a pumphead assembly and a motor assembly for driving the pumphead assembly in a new configuration, in which the pumphead and motor assembly are adjacent to, and laterally offset from, one another, thereby reducing the overall height of the device.

In accordance with a first aspect, an implantable drug infusion device includes a pumphead assembly having a drive shaft; and a motor assembly operably connected to the drive shaft. The motor assembly is adjacent the pumphead assembly in a radial direction with respect to the drive shaft.

In accordance with another aspect, an implantable drug infusion device includes a bulkhead having a race, a first chamber and a second chamber. A pump tube has an inlet and an outlet and is positioned within the race. A pumphead assembly has a drive shaft and is located within the first chamber. A motor assembly is located within the second chamber and is operably connected to the drive shaft of the pumphead assembly. The motor assembly is adjacent the pumphead assembly in a radial direction with respect to the drive shaft.

From the foregoing disclosure, it will be readily apparent to those skilled in the art, that is, those who are knowledgeable or experienced in this area of technology, that the present invention provides a significant advance over the prior art. Preferred embodiments of the implantable infusion device of the present invention can significantly reduce the overall height of the apparatus as compared to prior implantable pumps, and minimize discomfort to the patient. These and additional features and advantages of the invention disclosed here will be further understood from the following detailed disclosure of preferred embodiments.

BRIEF DESCRIPTION OF THE DRAWINGS

Preferred embodiments are described in detail below with reference to the appended drawings. The accompanying drawings, which are incorporated into and form a part of this specification, illustrate several embodiments of the present invention and, together with the description, serve to explain the principles of the invention. The above mentioned and other advantages and features of the invention will become apparent upon reading the following detailed description and referring to the accompanying drawings in which like numbers refer to like parts throughout and in which.

DESCRIPTION OF THE PREFERRED EMBODIMENT

Figure 1:
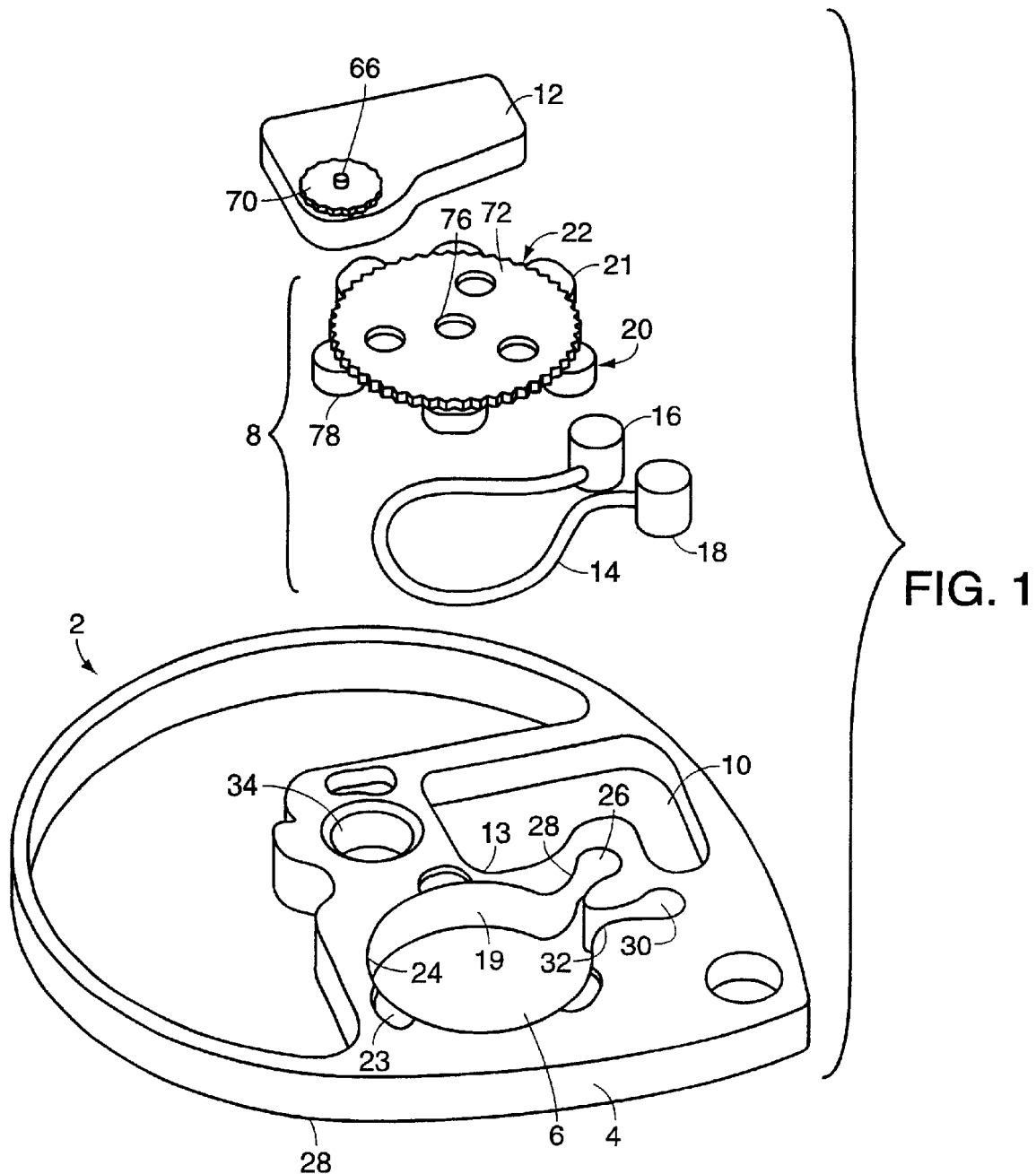
FIG. 1 is an exploded perspective view of an implantable drug infusion device in accordance with the present invention.

As shown in FIG. 1, an implantable drug infusion device 2 in accordance with the invention comprises a bulkhead 4 containing a number of chambers and cavities sized and configured to house various subsystems of the implantable drug infusion device. In particular, bulkhead 4 has a first chamber 6 sized and configured to house a peristaltic pumphead assembly 8. A second chamber 10, sized and configured to house a motor assembly 12 which drives pumphead assembly 8, is positioned adjacent first chamber 6 and separated therefrom by a wall 13. Other chambers of bulkhead 4 house a battery and the electronic circuitry (not shown) used to operate implantable drug infusion device 2 and to control the dosage rate of the medication into the body.

Pumphead assembly 8 includes a peristaltic pump tube 14 having an inlet 16 and an outlet 18, a compression member, such as roller assembly 20, for compressing tube 14, and a pump drive assembly 22 to operate the roller assembly. First chamber 6 has a generally circular wall 24 defining a pump race 19. Pump tube 14 is placed in first chamber 6 in close proximity to wall 24 so that roller assembly 20 may force the tube against the wall, thereby forcing medication to move through the tube in a known peristaltic manner. Flanges 21 extending outwardly from pump drive assembly 22 are received in recesses 23 formed in first chamber 6, supporting pump drive assembly 22 in first chamber 6. Inlet 16 is placed in a pump inlet cavity 26 formed in bulkhead 4. Pump inlet cavity 26 is connected to the pump race 19 by a pump inlet race ramp 28. Pump tube outlet 18 is placed in a pump outlet cavity 30 formed in bulkhead 4. Pump tube outlet cavity 30 is connected to the pump race 19 by a pump outlet race ramp 32. In a preferred embodiment, both pump inlet race ramp 28 and pump outlet race ramp 32 have an arcuate geometry. A cover (not shown) is also provided for bulkhead 4 to provide protection for the components of drug infusion device 2.

Bulkhead 4 has an integral fill port cavity 34, sized and configured to house a septum and components to retain the septum. Drugs are injected through the septum to fill a reservoir 35, seen in FIG. 4, formed by bellows 37 within a lower portion of bulkhead 4. A pathway is formed between the reservoir and pump inlet cavity 26, through which drugs are introduced into pump tube 14. The drugs exit pump outlet cavity 30 and travel through another pathway formed in bulkhead 4 to a catheter port on the periphery of bulkhead 4 from which the drug exits the device 2 and enters the anatomy of the individual. The structure of the septum, retaining components, pathways, and catheter port are known to one of skill in the art and are not shown here.

The specific size and shape of first chamber 6, second chamber 10, and the other chambers in bulkhead 4 will depend on the size and shape of the specific pump assembly, motor, and battery and electronics chosen for use in the implantable drug delivery device. Additionally, the pump inlet cavity 26, pump inlet race ramp 28, pump outlet cavity 30, and pump outlet race ramp 32 may be rendered unnecessary depending on the choice of pump assembly. In such an embodiment, first chamber 6 would be provided with an inlet means for creating a fluid pathway between the drug reservoir (either directly or indirectly) and first chamber 6, and an outlet means for creating a fluid pathway (either directly or indirectly) between first chamber 6 and a catheter port. Suitable inlet and outlet means may include passageways, conduits, orifices, bores, channels, walls, tubes or other known structures suitable for directing the flow of a fluid. Accordingly, the drawings are only illustrative of the preferred embodiments of the invention and the applicants contemplate bulkheads sized and configured differently than as shown as being within the scope of their invention.

Figure 2:
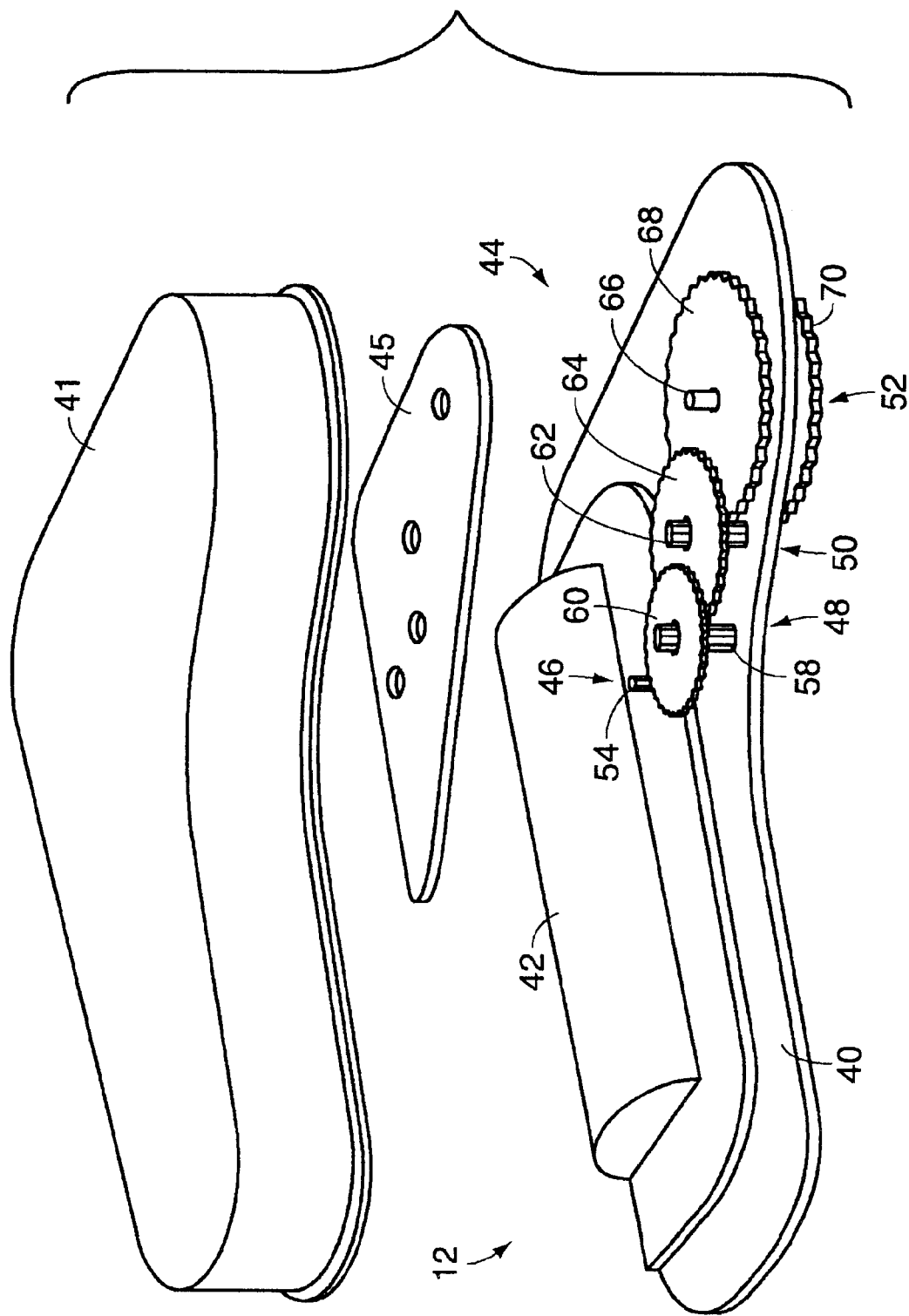
FIG. 2 is a bottom perspective view, in exploded form, of a motor assembly of the implantable device of FIG. 1.

Referring now to FIG. 2, motor assembly 12 is shown in exploded form in an inverted position. Motor assembly 12 is formed of plate 40 and housing 41. Motor 42 and motor drive assembly 44 are secured to plate 40. In a preferred embodiment, motor 42 is a stepper motor, but other motors, e.g., DC motors, will be suitable for driving pumphead assembly 8. In the illustrated embodiment, motor drive assembly 44 comprises a four-stage gear drive formed of first gear assembly 46, second gear assembly 48, third gear assembly 50, and fourth gear assembly 52. The gear assemblies are supported at lower ends thereof by bearings (not shown) on a bridge 45. First gear assembly 46 comprises a teethed shaft 54. Second gear assembly 48 comprises a teethed gear wheel 60 secured to a teethed shaft 58. Third gear assembly 50 comprises a teethed gear wheel 64 secured to a teethed shaft 62. Fourth gear assembly 52 comprises a shaft 66 to which are secured a lower teethed gear wheel 68 and an upper teethed gear wheel 70.

Figure 3:
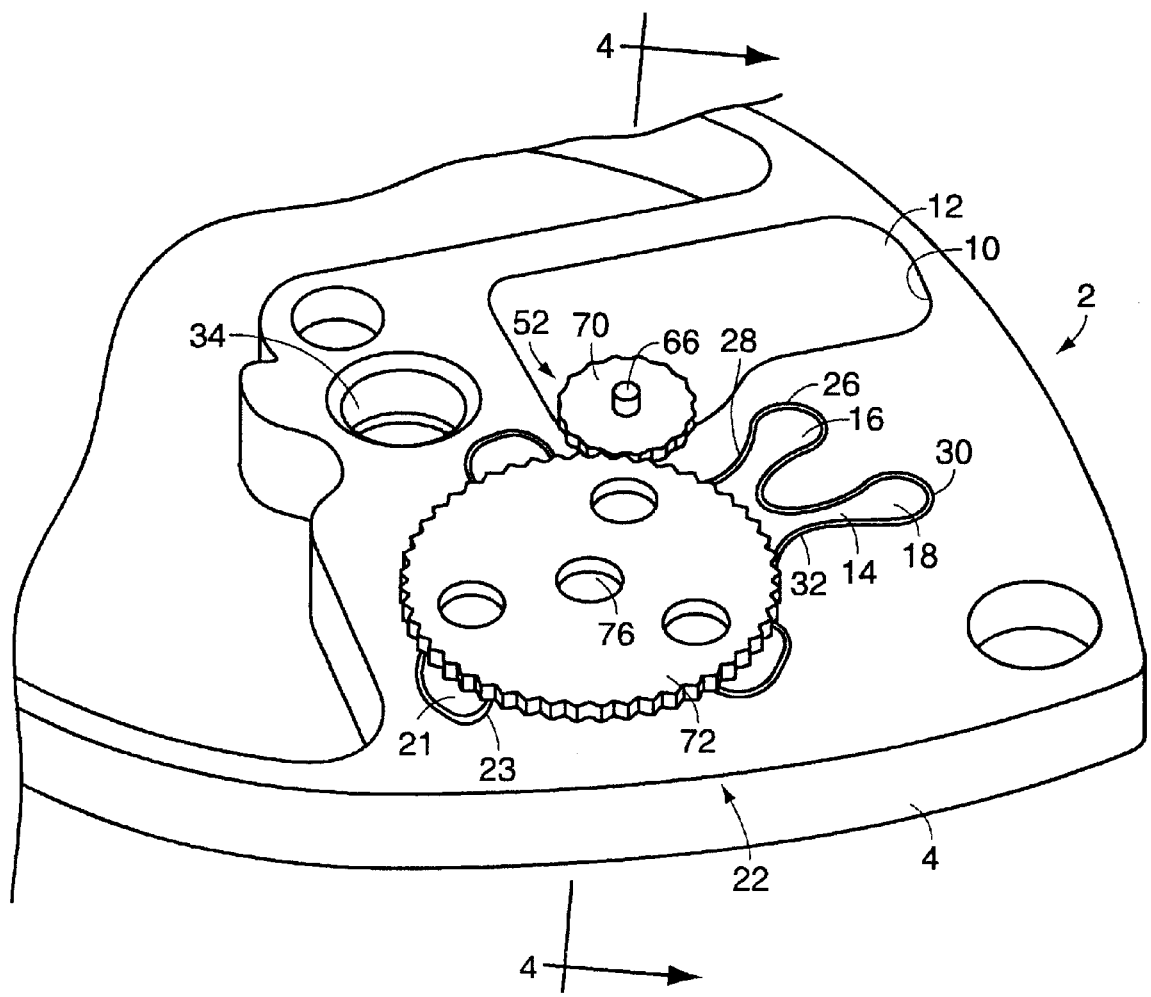
FIG. 3 is perspective view, partially cut away, of the implantable device of FIG. 1, shown in its assembled state.

Drug infusion device 2 is seen in its assembled state in FIG. 3, with motor assembly 12 positioned within second chamber 10, and pumphead assembly 8 positioned within first chamber 6.

A teethed pumphead gear 72 on pump drive assembly 22 meshes with upper gear wheel 70 of motor assembly 12.

Figure 4:
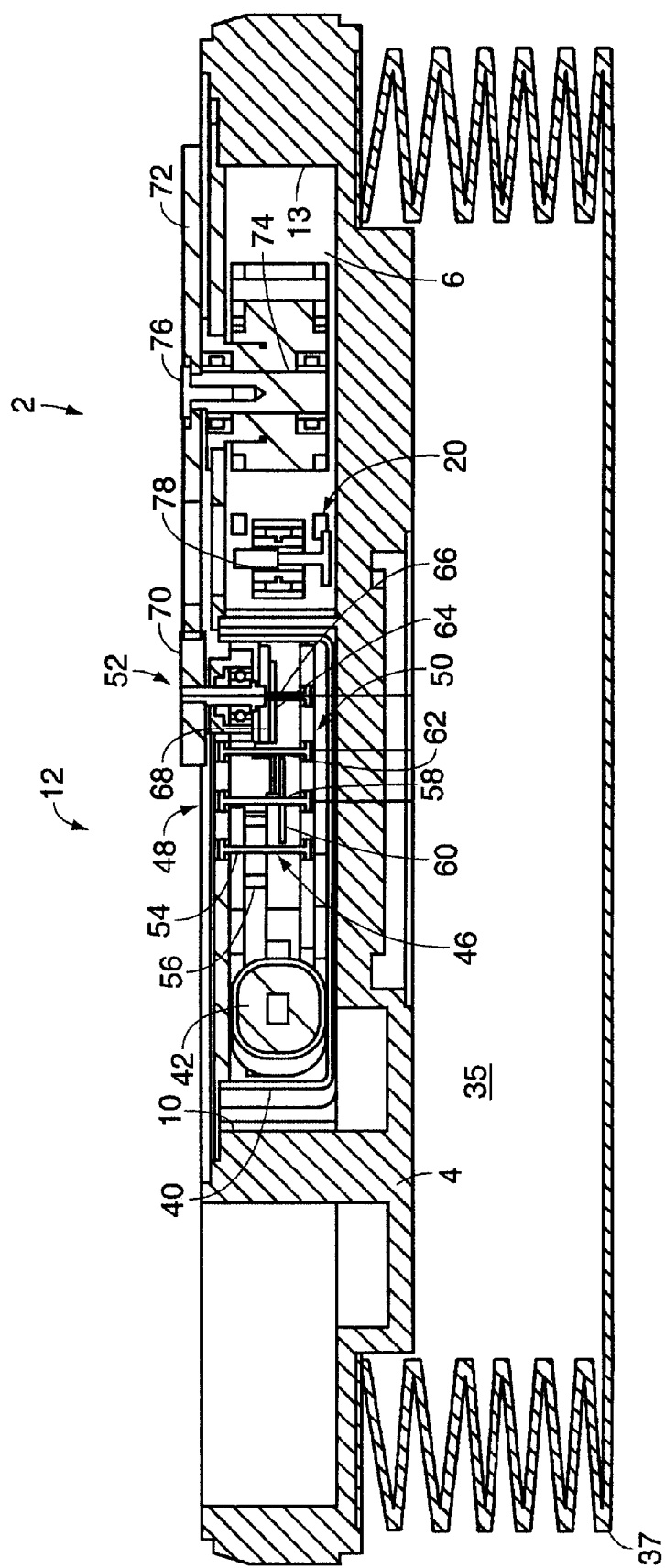
FIG. 4 is a section view, taken along lines 4—4 of FIG. 3, of the implantable device of FIG. 1.

During operation of the drug infusion device 2, as seen in FIGS. 2 & 4, a rotor 56 of motor 42 rotatably drives shaft 54, which in turn drivingly engages teethed gear wheel 60 of second gear assembly 48. Shaft 58 of second gear assembly 48 then drivingly engages teethed gear wheel 64 of third gear assembly 50. Shaft 62 of third gear assembly 50 then drivingly engages lower teethed gear wheel 68 of fourth gear assembly 52. Upper gear wheel 70 of fourth gear assembly 52 in turn drives pumphead gear 72, which is secured to a shaft 74 of pump drive assembly 22 by a retaining screw 76. Shaft 74 drives rollers 78 of roller assembly 20 around the pump race 19, compressing tube 14 and a forcing the drug therethrough in known peristaltic fashion.

Figure 5:
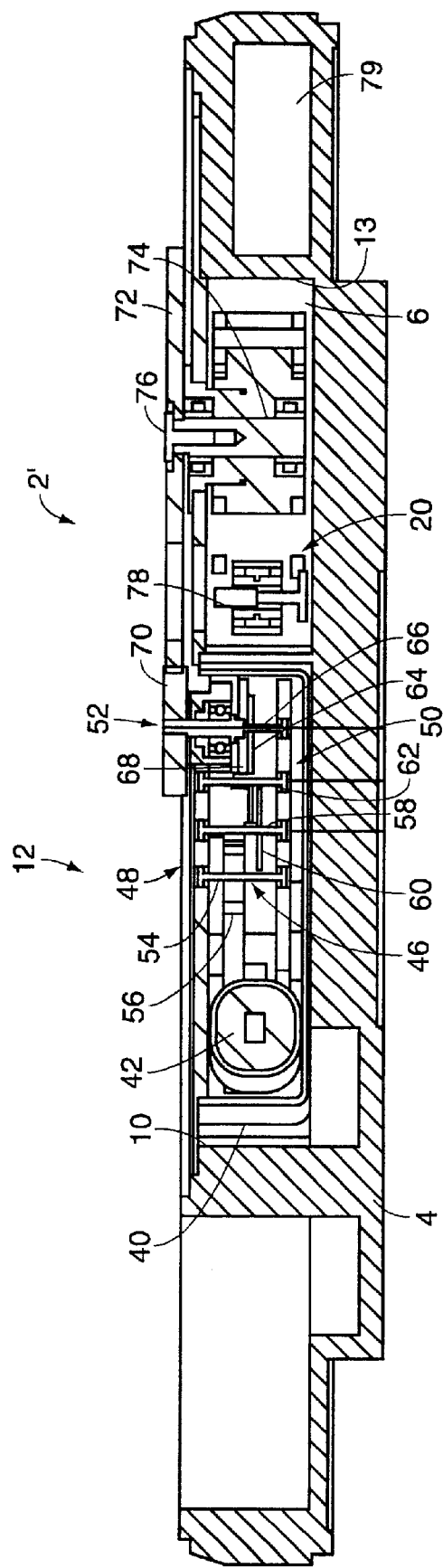
FIG. 5 is a section view of an alternative embodiment of the implantable device of FIG. 1.

Another embodiment of a drug infusion device 2' is shown in FIG. 5. In this embodiment, reservoir 79 is laterally offset from motor assembly 12 and pumphead assembly 8. By positioning reservoir 79 laterally offset from motor assembly 12 and pumphead assembly 8, rather than beneath them, the height of device 2' can be reduced even further.

It is to be appreciated that other motor drive assembly constructions will be suitable, and are considered within the scope of the present invention including, but not limited to, belt drive assemblies, chain drive assemblies, and friction drive assemblies. Other pumphead drive assemblies are also considered within the scope of the invention, and suitable pumphead drive assemblies will be readily apparent to those skilled in the art given the benefit of this disclosure.

Advantageously, under the present invention, the motor assembly is adjacent to and laterally offset from, the pumphead assembly, thereby reducing the overall height of the drug infusion device. In certain preferred embodiments, the motor assembly is radially adjacent the pumphead assembly with respect to the drive shaft of the pumphead. Locating the motor assembly adjacent the pumphead assembly provides a lower overall height than prior art implantable pumps which have the motor disposed coaxially with the pumphead assembly, that is, pumps having a drive shaft of the motor extending coaxially with a drive shaft of the pumphead. In a preferred embodiment, the overall height of the implantable drug infusion device 2 is preferably less than 7.2 millimeters.

Another advantage of the present design is the fact that motor assembly 12 and pumphead assembly 8 are separate units. This allows testing and calibration of the pumphead assembly independent of the motor. For example, the input torque required to drive the pumphead assembly can be measured without including the motor drag. Thus, pumphead assemblies with particular input torque requirements can be matched with appropriate motors having a matched torque output, providing manufacturing flexibility. Sterilization of the device can be completed when the pumphead and motor assembly are assembled, or the pumphead can be sterilized prior to assembly with the motor assembly.

In light of the foregoing disclosure of the invention and description of the preferred embodiments, those skilled in this area of technology will readily understand that various modifications and adaptations can be made without departing from the scope and spirit of the invention. All such modifications and adaptations are intended to be covered by the following claims.

What is claimed is:

1. An implantable drug infusion device comprising, in combination:
    a race; a pumphead assembly having a gear connected to a drive shaft;
    a motor assembly having a housing, a motor positioned within the housing, a gear assembly comprising a plurality of gears and positioned within the housing, and a gear outside the housing that is driven by the gear assembly and engages the gear of the pumphead assembly;
    the motor housing being adjacent the race in a radial direction with respect to the drive shaft.

2. The implantable drug infusion device of claim 1, wherein the pumphead assembly comprises a peristaltic pump.

3. The implantable drug infusion device of claim 1, wherein the gear assembly comprises a first gear driven by the motor, a second gear driven by the first gear, and a third gear driven by the second gear, the gear outside the motor housing being driven by the third gear.

4. The implantable drug infusion device of claim 3, wherein the first gear comprises a teethed shaft, and each of the second gear and third gear comprise a teethed shaft and a teethed gear wheel secured to the shaft.

5. The implantable drug infusion device of claim 4, wherein the gear outside the motor housing includes a shaft extending into the motor housing, an upper teethed gear wheel secured to the shaft, and a lower teethed gear wheel positioned inside the housing and secured to the shaft, and the gear of the pumphead assembly is a teethed gear wheel secured to the drive shaft, wherein the lower teethed gear wheel is driven by the teethed gear wheel of the third gear, and the upper teethed gear wheel drives the gear of the pumphead assembly.

6. The implantable drug infusion device of claim 1, wherein the pumphead assembly includes a pump tube and a plurality of rollers rotatably driven by the drive shaft to compress the pump tube.

7. An implantable drug infusion device comprising, in combination:
    a bulkhead having a first chamber including a race and a second chamber;
    a pump tube having an inlet and an outlet and being positioned within the race;
    a pumphead assembly having a gear connected to a drive shaft and being positioned within the first chamber; and
    a motor assembly having a housing that is positioned within the second chamber, a motor positioned within the housing, a gear assembly comprising a plurality of gears and positioned within the housing, and a gear outside the motor housing that is driven by the gear assembly and engages the gear of the pumphead assembly;
    wherein the motor housing is adjacent the race in a radial direction with respect to the drive shaft.

8. The implantable drug infusion device of claim 7, wherein the pumphead assembly includes a plurality of rollers rotatably driven by the drive shaft and oriented to compress the pump tube.

9. The implantable drug infusion device of claim 7, wherein the gear assembly comprises a first gear driven by the motor, a second gear driven by the first gear, and a third gear driven by the second gear, the gear outside the motor housing being driven by the third gear.

10. The implantable drug infusion device of claim 7, wherein the pumphead comprises a plurality of rollers rotatably driven by the drive wheel and oriented to compress the pump tube.

11. An implantable drug infusion device comprising, in combination:
    a race;
    a pumphead assembly having a gear connected to a drive shaft; and
    a motor assembly having a housing, a motor positioned within the housing, a gear assembly comprising a plurality of gears and positioned within the housing, and a gear outside the housing that is driven by the gear assembly and engages the gear of the pumphead assembly, the motor assembly being adjacent to and laterally offset from the race.

12. The implantable drug infusion device of claim 11, further comprising a reservoir, the reservoir being laterally offset from the pumphead assembly and the motor assembly.

13. An implantable drug infusion device having a thickness in a first direction and a width in a direction perpendicular to the first direction, the implantable drug infusion device comprising:
    a pump assembly comprising:
        a pump having a thickness in the first direction; and
        a motor operably connected to the pump, the motor having a thickness in the first direction,
        the motor and pump being arranged in a side-by-side manner generally perpendicular to the first direction, the motor and pump having an overall thickness in the first direction no greater than either the thickness or the thickness of the pump; and a reservoir adjacent the pump assembly in the first direction such that the reservoir and pump assembly are arranged in a side-by-side manner along the first direction.

14. The implantable drug infusion device of claim 13, wherein the pump has a drive shaft driven by a drive shaft of the motor.

15. The implantable drug infusion device of claim 14, wherein the drive shafts of the motor and the pump each have an axial direction extending parallel to the first direction.

16. The implantable drug infusion device of claim 14, wherein the motor includes a plurality of gears, the gears operably connected to drive the drive shaft of the pump.

17. The implantable drug infusion device of claim 16, further including a motor housing.

18. The implantable drug infusion device of claim 17, wherein the gears are contained within the motor housing.

19. The implantable drug infusion device of claim 13, wherein the pump comprises a peristaltic pump.

20. An implantable drug infusion device having a thickness in a first direction and a width in a direction perpendicular to the first direction, the implantable drug infusion device comprising:

an pump assembly comprising:
  a motor; and
  a pump operably connected to the motor;
  the motor and pump being arranged in a side-by-side manner generally perpendicular to the first direction; and a reservoir adjacent the pump assembly in the first direction such that the reservoir and pump assembly are arranged in a side-by-side manner along the first direction.

21. The implantable drug infusion device of claim 20, wherein the pump has a drive shaft driven by a drive shaft of the motor.

22. The implantable drug infusion device of claim 21, wherein the drive shafts of the motor and the pump have an axial direction parallel to the first direction.

23. The implantable drug infusion device of claim 21, wherein the motor includes a plurality of gears, the gears operably connected to drive the drive shaft of the pump.

24. The implantable drug infusion device of claim 23, further including a motor housing.

25. The implantable drug infusion device of claim 24, wherein the gears are contained within the motor housing.

26. The implantable drug infusion device of claim 20, wherein the pump comprises a peristaltic pump.

* * * * *